United States Patent [19]

Kropp

[11] 4,008,073
[45] Feb. 15, 1977

[54] ALLOY POWDER FOR THE PRODUCTION OF DENTAL AMALGAM

[75] Inventor: Rudolf Kropp, Pforzheim-Wurm, Germany

[73] Assignee: Deutsche Gold- und Silber-Scheideanstalt vormals Roessler, Frankfurt, Germany

[22] Filed: Nov. 18, 1975

[21] Appl. No.: 632,953

[30] Foreign Application Priority Data

Mar. 14, 1975 Germany .......................... 2511194

[52] U.S. Cl. .................. 75/.5 R; 75/169; 75/173 C
[51] Int. Cl.² .......................................... C22C 5/08
[58] Field of Search ................ 75/173 C, .5 R, 169

[56] References Cited

UNITED STATES PATENTS

| | | | |
|---|---|---|---|
| 3,305,356 | 2/1967 | Youdelis | 75/173 C X |
| 3,841,860 | 10/1974 | Wolf | 75/.5 R |
| 3,871,876 | 3/1975 | Asgar | 75/169 |
| 3,901,693 | 8/1975 | Wolf | 75/169 |

*Primary Examiner*—L. Dewayne Rutledge
*Assistant Examiner*—E. L. Weise
*Attorney, Agent, or Firm*—Cushman, Darby & Cushman

[57] ABSTRACT

Alloy powders suitable for the production of dental amalgams are prepared containing 75–92% silver, 8–23% copper, 1–10% tin and 0–2% zinc.

8 Claims, No Drawings

ALLOY POWDER FOR THE PRODUCTION OF DENTAL AMALGAM

The invention is directed to alloy powders suitable for the production of dental amalgams which after mixing with mercury provide a plastic paste which can be used to fill cavities in teeth and harden after placing the filling in the mouth.

There are known powders produced by milling or jet blasting which have a particle size below <0.15 mm, a silver content between 50 and 75%, a tin content between 25 and 50%, copper content up to 6%, zinc content up to 2% and mercury content up to 3% and which have long been found of value in dentistry. However, these alloy powders have the disadvantage that in the hardening of the paste mixed with mercury there is formed in addition to a silver-mercury phase a practically silver free phase of the composition $Sn_{7-8}Hg$ which in the literature is designated $\gamma_2$. This tin rich phase is relatively susceptible to corrosion and fixes the electrochemical potential of the entire amalgam filling which through this corresponds about to that of pure tin. Furthermore the mechanical properties of the amalgam filling are also influenced disadvantageously by the $\gamma_2$ phase. Therefore, for a long time there have been efforts to avoid the formation of the $\gamma_2$ phase by increasing the silver content and lowering the tin content. However, alloys with silver contents over 75% in the hardening with mercury exhibit setting expansion which is substantially higher than the maximum of 0.2% permitted in the pertinent specification. Therefore, they are useless.

It is known that by addition of 2–20% palladium the setting expansion can be brought into the desired lower range, Kucher German Pat. No. 1,215,865, Rohm U.S. Pat. No. 3,141,761. However, the addition of palladium increases the expense of the alloy considerably. Another way to $\gamma_2$ free amalgams with lower setting expansion is by the addition of up to 50% of tinfree silver-copper alloy powders to the customary, tin containing powders (Youdelis U.S. Pat. No. 3,305,356) or by mixing 50–90% of a type of powder containing over 15% copper with 10–50% of a type of powder of the previously customary alloys (Wolf U.S. Pat. No. 3,841,860). However, in both cases the lowering of the tin content is only obtained by increasing the copper content while the silver content remains substantially unchanged. However, there is desired an alloy with a distinctly increased silver content with a simultaneous corresponding reduction in the portion of non-noble additive, especially tin, to increase the corrosion resistance.

Therefore, it was the problem of the present invention to find a silver rich and tin poor alloy powder for the production of dental alloys which does not form a $\gamma_2$ phase, whose setting expansion is within the pertinent specifications and whose mechanical properties at least are as good as the previously used alloy powders.

This problem was solved by the invention by using an alloy which contains 75–92 weight % silver, 8–23 weight % copper, 1–10 weight % tin and 0–2 weight % zinc.

It has been surprisingly found that alloys with silver contents above 75% show no increased setting expansion in the setting with mercury if there is included in the alloy at least 8–10% of copper, wherein in order to still further improve the industrial properties several percentages of tin are added, but in no case above 10%. Furthermore, the alloys can contain zinc in an amount up to 2%. The production of such alloy powders can take place by milling or lathing cast ingots or by atomizing the melt. The chips obtained in the first named process can be comminuted further by a grinding process.

It was established that amalgams produced from the powders of the invention not only are free of $\gamma_2$ phase but also have a very low creep behavior. The plastic deformation of a hardened amalgam under constant load in the present alloys is about an entire power of 10 lower than the customary amalgams with higher tin and lower silver contents. This has the advantage that fillings of an amalgam produced with the alloy powder of the invention are substantially less deformed by the constant chewing pressure in the mouth in the course of time than fillings of the previously used amalgams. Thereby there is substantially less danger of taking off the marginal filling edges and their subsequent breaking. Additionally the setting expansion of amalgams produced with alloy powders of the invention lies within the pertinent specifications.

As examples of alloys within the invention which after pulverization, mixing with mercury and hardening have the mentioned lower values for the setting expansion and the creep there are mentioned the following compositions in Table 1.

Unless otherwise indicated all parts and percentages are by weight.

TABLE 1

| SILVER (WEIGHT %) | COPPER (WEIGHT %) | TIN (WEIGHT %) | ZINC (WEIGHT %) |
|---|---|---|---|
| 90 | 8 | 2 | 0 |
| 85 | 10 | 5 | 0 |
| 82 | 10 | 8 | 0 |
| 80 | 15 | 5 | 0 |
| 76 | 18 | 5 | 1 |

The over-all composition of the alloy powder of the invention containing 75–92 weight % silver, 8–23 weight % copper and 1–10 weight % tin, however, can also be attained by mixing alloy powders of different compositions in which there is used as the main constituent a high silver containing powder with or without a little tin and adding a smaller amount of a powder having a higher tin content. Approved are mixtures in which one component is present in an amount of 60 to 95 weight % and consists of 80–92 weight % silver, 8–20 weight % copper, 0–8 weight % tin and 0–2 weight % zinc, while the other component which is 40 to 5 weight % consists of 50–75 weight % silver, 0–25 weight % copper, 20–50 weight % tin and 0–2 weight % zinc. An alloy powder containing zinc can contain, for example, 75–92% silver, 8–23% copper, 1–10% tin and 0.2 to 2% zinc. The mixing of the mentioned two different powders gives the possibility to optimize the values of some technical properties e.g. compressive strength and tensile strength exceeding those of one component powders. Furthermore it is known to combine the advantages of spherical alloys as the possibility of condensing the amalgam with lower force with the advantage of cut alloys as the good body of the amalgam by mixing both types of powders. Therefore another advantage can be attained by mixing two powders differing not only in their composition but also in the shape and the size of their particles.

In Table 2 several examples of such mixtures are given.

TABLE 2

| COMPONENT 1 | | | | COMPONENT 2 | | | | |
|---|---|---|---|---|---|---|---|---|
| Portion | Composition | | | Portion | Composition | | | |
| (Wt. %) | Ag (Wt. %) | Cu (Wt. %) | Sn (Wt. %) | (Wt. %) | Ag (Wt. %) | Cu (Wt. %) | Sn (Wt. %) | |
| 80 | 90 | 10 | 0 | 20 | 70 | 5 | 25 | |
| 90 | 86 | 12 | 2 | 10 | 60 | 0 | 40 | |
| 70 | 90 | 10 | 0 | 30 | 60 | 15 | 25 | |
| 66 | 80 | 20 | 0 | 34 | 71 | 3 | 25 | Zn |
| 90 | 90 | 10 | 0 | 10 | 60 | 5 | 33 | 2 |

The components of these mixtures can be produced for example by milling of correspondingly composed bars or by atomizing of a corresponding melt. However, it is also possible to produce only one of the components by milling and the other by atomization.

The alloy powders produced exhibit outstanding mechanical properties and are very easily worked.

The compositions of the invention can consist essentially of or consist of the materials set forth.

What is claimed is:

1. An alloy powder suitable for production of dental amalgams consisting essentially of 75–92% silver, 8–23% copper, 1–10% tin and zinc, the zinc being present in an amount up to 2%.

2. An alloy powder according to claim 1 containing 0.2 to 2% zinc.

3. An alloy powder suitable for production of dental amalgams consisting essentially of 75–92% silver, 8–23% copper, 1–10% tin and 0–2% zinc, said powder being a mixture of two separate alloy powder components, the first of which is 60–95% of the total and consists of 80–92% silver, 8–20% copper, 0–8% tin and 0–2% zinc, while the second of which is 40–5% of the total and consists of 50–75% silver, 0–25% copper, 20–50% tin and 0–2% zinc.

4. A method of producing the alloy powder of claim 3 comprising mixing two separate components, the first of which is 60–95% of the total and consists of 80–92% silver, 8–20% copper, 0–8% tin and 0–2% zinc while the second of which is 40–5% of the total and consists of 50–75% silver, 0–25% copper, 20–50% tin and 0–2% zinc.

5. A process according to claim 4 including the steps of producing the first component by atomizing a melt and producing the second component by milling an alloy bar.

6. An alloy powder suitable for production of dental amalgams consisting essentially of 90% silver, 8% copper and 2% tin.

7. An alloy powder suitable for production of dental amalgams consisting essentially of 85% silver, 10% copper and 5% tin.

8. An alloy powder suitable for production of dental amalgams consisting essentially of 82% silver, 10% copper and 8% tin.

* * * * *